United States Patent
Ogawa et al.

(10) Patent No.: US 9,707,200 B2
(45) Date of Patent: Jul. 18, 2017

(54) METABOLISM-IMPROVING AGENT COMPRISING RARE FATTY ACID

(71) Applicants: KYOTO UNIVERSITY, Kyoto-shi, Kyoto (JP); NITTO PHARMACEUTICAL INDUSTRIES, LTD., Muko-shi, Kyoto (JP)

(72) Inventors: Jun Ogawa, Kyoto (JP); Shigenobu Kishino, Kyoto (JP); Si-Bum Park, Kyoto (JP); Teruo Kawada, Kyoto (JP); Nobuyuki Takahashi, Kyoto (JP); Tsuyoshi Goto, Kyoto (JP); Hidekazu Kim, Kyoto (JP); Tatsuya Sugawara, Kyoto (JP); Takashi Hirata, Kyoto (JP); Yasunori Yonejima, Muko (JP)

(73) Assignees: Kyoto University, Kyoto (JP); Nitto Pharmaceutical Industries, Ltd., Kyoto (JP)

( * ) Notice: Subject to any disclaimer, the term of this patent is extended or adjusted under 35 U.S.C. 154(b) by 0 days.

(21) Appl. No.: 14/439,146

(22) PCT Filed: Oct. 14, 2013

(86) PCT No.: PCT/JP2013/077871
§ 371 (c)(1),
(2) Date: Apr. 28, 2015

(87) PCT Pub. No.: WO2014/069227
PCT Pub. Date: May 8, 2014

(65) Prior Publication Data
US 2015/0342916 A1 Dec. 3, 2015

(30) Foreign Application Priority Data
Oct. 29, 2012 (JP) ................. 2012-237933

(51) Int. Cl.
A61K 31/20 (2006.01)
A61K 31/201 (2006.01)
A61K 31/202 (2006.01)
A23K 20/158 (2016.01)
A23L 33/12 (2016.01)

(52) U.S. Cl.
CPC .......... A61K 31/202 (2013.01); A23K 20/158 (2016.05); A23L 33/12 (2016.08); A61K 31/20 (2013.01); A61K 31/201 (2013.01)

(58) Field of Classification Search
IPC .......................................... A61K 31/201,31/20
See application file for complete search history.

(56) References Cited

U.S. PATENT DOCUMENTS

| | | | |
|---|---|---|---|
| 4,582,804 A | 4/1986 | Litchfield et al. | |
| 7,015,249 B1 * | 3/2006 | Vanden Heuvel | A61K 31/20 514/560 |
| 2004/0019109 A1 | 1/2004 | Owman et al. | |
| 2006/0217441 A1 | 9/2006 | Akimoto et al. | |
| 2010/0305012 A1 | 12/2010 | Miyamoto et al. | |
| 2015/0125911 A1 | 5/2015 | Ogawa et al. | |

FOREIGN PATENT DOCUMENTS

| | | |
|---|---|---|
| EP | 1481671 A1 | 12/2004 |
| JP | 2006-521368 A | 9/2006 |
| JP | 2007-259712 A | 10/2007 |
| JP | 2009-051732 A | 3/2009 |
| JP | 2009-209054 A | 9/2009 |
| JP | 2011-184411 A | 9/2011 |
| KR | 10-0824969 B1 | 4/2008 |
| WO | WO 99/16435 * | 4/1999 |
| WO | WO 9916435 * | 4/1999 |
| WO | WO 02/00042 A2 | 1/2002 |
| WO | WO 2009/096570 A1 | 8/2009 |
| WO | WO 2012/032415 A2 | 3/2012 |
| WO | WO 2012/032417 A2 | 3/2012 |
| WO | WO 2013/168310 A1 | 11/2013 |

OTHER PUBLICATIONS

Kidshealth.org (2013).*
Simmons et al. Acta Diabetol. 1993; 30(4);233-7 (Abstract.*
Nagao K, *J. Biosci. Bioeng.*, 100(2): 152-157 (2005).
Kim et al., *Mol. Nutr. Food Res.*, 55: 585-593 (2011).
Kim et al., *PLoS ONE*, 7(2): e31317 (2012).
Kishino et al., *Biochem. Biophys. Res. Commun.* 416(1-2): 188-193 (2011).
Japanese Patent Office, International Search Report in International Patent Application No. PCT/JP2013/077871 (Jan. 21, 2014).
Duran-Sandoval et al., "PPAR agonists in the treatment of the metabolic syndrome and type 2 diabetes" in Gaw, A. and Shepherd, J., eds., *Lipids and Atherosclerosis Annual 2003* (Taylor & Francis, Ltd., London, U.K., 2003), pp. 37-57.
European Patent Office, Supplementary European Search Report in Application No. 13850683 (Apr. 14, 2016).
European Patent Office, Communication Pursuant to Rule 114(2) EPC in European Patent Application No. 13850683.7 (Dec. 7, 2016).

* cited by examiner

*Primary Examiner* — Shirley V Gembeh
(74) *Attorney, Agent, or Firm* — Leydig, Voit & Mayer, Ltd.

(57) ABSTRACT

The present invention provides a metabolism improving agent comprising an oxo fatty acid having 18 carbon atoms and a carbonyl group at the 10- or 12-position, and/or a hydroxy fatty acid having 18 carbon atoms and a hydroxyl group at the 10- and/or 12-position(s), and use of the metabolism improving agent as a food, a pharmaceutical product and the like.

20 Claims, 8 Drawing Sheets influence on immature SREBP-1 expression induced by LXR agonist influence on mature SREBP-1 expression induced by LXR agonist influence on SCD-1 mRNA expression induced by LXR agonist influence on FAS mRNA expression induced by LXR agonist

US 9,707,200 B2

METABOLISM-IMPROVING AGENT COMPRISING RARE FATTY ACID

CROSS-REFERENCE TO RELATED APPLICATIONS

This patent application is the U.S. national phase of International Patent Application No. PCT/JP2013/077871, filed Oct. 14, 2013, which claims the benefit of Japanese Patent Application No. 2012-237933, filed on Oct. 29, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 7,679 bytes ASCII (Text) file named "720633ReplacementSequenceListing.txt," created Jun. 23, 2015.

TECHNICAL FIELD

The present invention relates to a metabolism improving agent containing a rare fatty acid. More particularly, the present invention relates to a metabolism improving agent utilizing the physiological function, for example, effect of improving metabolism of lipid, sugar and energy, of rare fatty acids such as oxo fatty acid, hydroxy fatty acid and the like. The present invention also relates to a food, a pharmaceutical product, a feed and the like containing the agent.

BACKGROUND ART

In recent years, obesity due to overeating, shortage of exercise and the like, particularly lifestyle-related disease accompanying accumulation of visceral fat, has become a social problem. Metabolic syndrome refers to a condition where at least two of hyperglycemia, hypertension and lipid abnormality are complicated and arteriosclerosis is easily developed due to visceral fat obesity. In Japanese people at the age of 40-74, one in two in male and one in five in female are estimated to have or potentially have metabolic syndrome. Therefore, the importance of adjustment of ingestion calorie by diet therapy with the aim of preventing or solving progress of lipid accumulation in metabolic syndrome has been proposed.

There is considerable interest in ingestion, in dining, of functional lipids reported to have a lipid metabolism improving effect, a diabetes improving effect and the like, including conjugated fatty acids such as conjugated linoleic acid and the like (non-patent document 1), ω3 polyunsaturated fatty acids such as eicosapentaenoic acid, docosahexaenoic acid and the like (patent document 1), medium chain fatty acid (patent document 2) and the like.

In addition, it has been reported in recent years that a part of oxo fatty acids such as 9-oxo-octadecadienoic acid, 13-oxo-octadecadienoic acid and the like contained in tomato have an activity to improve lifestyle-related diseases, such as lipid metabolism improvement and the like (patent document 3, non-patent documents 2, 3). Therefore, the physiological functions of rare fatty acids such as oxo fatty acid, hydroxy fatty acid and the like are also drawing attention.

However, more detailed physiological function of variously existing rare fatty acids is not known.

DOCUMENT LIST

Patent Documents patent document 1: JP-A-2006-521368
patent document 2: WO 2009/096570
patent document 3: JP-A-2011-184411

Non-Patent Documents non-patent document 1: Nagao K, (2005), J. Biosci. Bioeng., vol. 100, no. 2, p. 152-157
non-patent document 2: Kim Y-I, (2011), Mol. Nutr. Food Res., vol. 55, p. 585-593
non-patent document 3: Kim Y-I, (2012), PLoS ONE, vol. 7, no. 2, e31317

SUMMARY OF THE INVENTION

Problems to be Solved by the Invention

An object of the present invention is to provide a novel metabolism improving agent containing a rare fatty acid, which improves the metabolism of lipid and/or sugar and the like.

Means of Solving the Problems

The present inventors have conducted intensive studies in view of the above-mentioned problem and found that oxo fatty acids, for example, 10-oxo-cis-12-octadecenoic acid (hereinafter to be also referred to as "KetoA"), or hydroxy fatty acid, for example, 10-hydroxy-cis-12-octadecenoic acid (hereinafter to be also referred to as "HYA"), has a peroxisome proliferator-activated receptor (hereinafter to be also referred to as "PPAR")-activating action, a blood glucose level increase-suppressive action, a blood neutral fat-lowering action, a glucose tolerance-improving action, an energy metabolism-promoting action and the like, which are conventionally-unknown physiological functions.

Furthermore, the present inventors have also found that rare fatty acids such as HYA, KetoA and the like have a suppressive action on the lipid synthesis promotion induced by a Liver X Receptor (hereinafter to be also referred to as "LXR") agonist.

The present invention was completed based on the above findings.

Accordingly, the present invention provides the following:

[1] A metabolism improving agent comprising an oxo fatty acid having 18 carbon atoms and a carbonyl group at the 10- or 12-position, and/or a hydroxy fatty acid having 18 carbon atoms and a hydroxyl group at the 10- and/or 12-position(s).
[2] The agent of [1], wherein the aforementioned oxo fatty acid and/or hydroxy fatty acid have/has a trans double bond at the 11-position, or a cis double bond at the 12-position.
[3] The agent of [1], wherein the oxo fatty acid is at least one kind selected from the group consisting of 10-oxo-cis-12-octadecenoic acid (KetoA), 10-oxo-cis-12,cis-15-octadecadienoic acid (αKetoA), 10-oxo-cis-6,cis-12-octadecadienoic acid (γKetoA), 10-oxo-cis-6,cis-12,cis-15-octadecatrienoic acid (sKetoA), 10-oxooctadecanoic acid (KetoB), 10-oxo-cis-6-octadecenoic acid (γKetoB), 10-oxo-cis-15-octadecenoic acid (αKetoB) or 10-oxo-cis-6,cis-15-octadecadienoic acid (sKetoB), 12-oxooctadecanoic acid (rKetoB), 10-oxo-trans-11-octadecenoic acid (KetoC), 10-oxo-cis-6,trans-11-octadecadienoic acid (γKetoC), 10-oxo-trans-11,cis-15-octadecadienoic acid (αKetoC), 10-oxo-cis-6,trans-11,cis-15-octadecatrienoic acid (sKetoC), and 12-oxo-cis-9-octadecenoic acid (KetoRA).

[4] The agent of [1], wherein the hydroxy fatty acid is at least one kind selected from the group consisting of 10-hydroxy-cis-12-octadecenoic acid (HYA), 10-hydroxy-cis-12,cis-15-octadecadienoic acid (αHYA), 10-hydroxy-cis-6, cis-12-octadecadienoic acid (γHYA), 10-hydroxy-cis-6,cis-12,cis-15-octadecatrienoic acid (sHYA), 10,12-dihydroxyoctadecanoic acid (rHYA), 10-hydroxyoctadecanoic acid (HYB), 10-hydroxy-cis-15-octadecenoic acid (αHYB), 10-hydroxy-cis-6-octadecenoic acid (γHYB), 10-hydroxy-cis-6,cis-15-octadecadienoic acid (sHYB), 12-hydroxyoctadecanoic acid (rHYB), 10-hydroxy-trans-11-octadecenoic acid (HYC), 10-hydroxy-trans-11,cis-15-octadecadienoic acid (αHYC), 10-hydroxy-cis-6,trans-11-octadecadienoic acid (γHYC), 10-hydroxy-cis-6,trans-11,cis-15-octadecatrienoic acid (sHYC), and ricinoleic acid (RA).

[5] The agent of any one of [1]-[4], which is used for the prophylaxis or improvement of at least one kind selected from the group consisting of obesity, diabetes, lipid metabolism abnormality, hyperlipidemia, and fatty liver.

[6] The agent of any one of [1]-[4], which is a food or a food additive.

[7] The agent of any one of [1]-[4], which is a pharmaceutical product.

[8] The agent of any one of [1]-[4], which is a feed or a feed additive.

[9] A method of improving metabolism in a mammal, comprising administering an oxo fatty acid having 18 carbon atoms and a carbonyl group at the 10- or 12-position, and/or a hydroxy fatty acid having 18 carbon atoms and a hydroxyl group at the 10- and/or 12-position(s) to the mammal.

[10] An oxo fatty acid having 18 carbon atoms and a carbonyl group at the 10- or 12-position, and/or a hydroxy fatty acid having 18 carbon atoms and a hydroxyl group at the 10- and/or 12-position(s) for use as a metabolism improving agent.

[11] Use of an oxo fatty acid having 18 carbon atoms and a carbonyl group at the 10- or 12-position, and/or a hydroxy fatty acid having 18 carbon atoms and a hydroxyl group at the 10- and/or 12-position(s) in the production of a metabolism improving agent.

In the present invention, "and/or" is used to mean any one of them or both of them.

Effect of the Invention

In the present invention, oxo fatty acid or hydroxy fatty acids such as KetoA or HYA (hereinafter to be also referred to as oxo fatty acid and the like) was found to have conventionally-unknown physiological functions, for example, a PPAR activating action, a blood glucose level increase-suppressive action, a blood neutral fat-lowering action, a glucose tolerance-improving action, an energy metabolism-promoting action and the like. Furthermore, they have also found that these oxo fatty acids, and the like have a strong lipid synthesis suppressive action due to an antagonizing action on LXR.

Based on such functions, the present invention provides a metabolism improving agent containing rare fatty acid oxo fatty acid and the like. Since the agent can be used in various fields such as pharmaceutical product, food, feed and the like, the present invention is industrially extremely useful.

DESCRIPTION OF EMBODIMENTS

Figure 1:
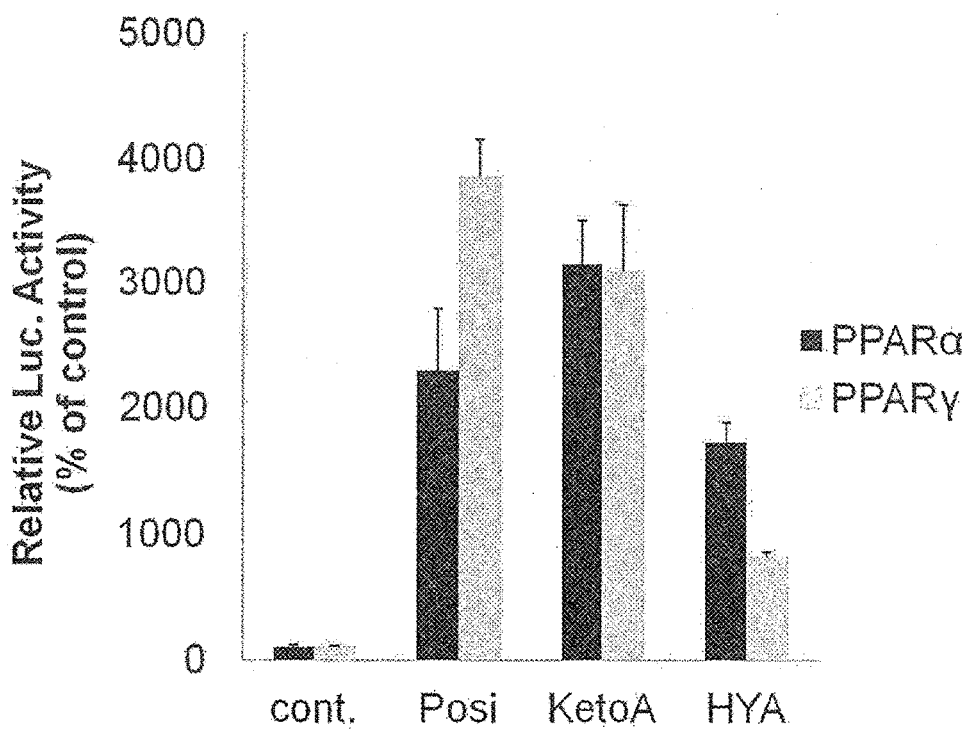
FIG. 1 shows the results of PPARα/γ reporter activity of KetoA or HYA, wherein cont. shows negative control (ethanol addition), Posi shows positive control (PPAR agonist addition), and the vertical axis shows relative luciferase activity.

The present invention is explained in detail below.

In the present invention, the "metabolism improvement" means that the metabolism of lipid and/or sugar and/or energy are/is improved. Specifically, for example, lipid metabolism improvement means promotion of the decomposition of lipid present in the body tissue, blood, or lymph tissue, suppression of lipid synthesis, prevention and/or suppression of accumulation of lipid in body tissues such as adipose tissue and the like, or reduction of lipid accumulated in body tissue and the like. The "lipid" is triglyceride and/or cholesterol, including fatty acid.

The improvement of sugar metabolism means suppression of an increase in sugar, and/or glycated hemoglobin (HbA1c) present in blood, fasting blood sugar level, or promotion of sugar metabolism after eating. Furthermore, sugar metabolism improvement also includes improvement of impaired glucose tolerance (pathology not included in normal type or diabetes type, and pre-diabetic). The "sugar" refers to monosaccharide, disaccharide or polysaccharide.

The improvement of energy metabolism means bringing the state of abnormal balance of ingested energy level and release energy level, or the state of unattainable control of the balance of ingested energy level and release energy level, to a normal state or closer to a normal state.

As an index of the aforementioned metabolism improvement, PPAR activity can be measured. It is known that PPAR includes at least 3 kinds of subtypes: PPARα, PPARδ (same as β) and PPARγ. PPARα is mainly expressed in the liver, heart, kidney, skeletal muscle, brown adipocyte and the like, and is involved in control of many genes relating to β oxidation of fatty acid. PPARδ is expressed in comparatively all over the body (brain, adipose tissue, skin etc.). PPARγ has at least 3 kinds of isoforms, is mainly expressed in white adipocyte and macrophage, and is involved in adipocyte differentiation and the like. When the presence or absence of a ligand (agonist, antagonist) activity is confirmed for at least one kind of these PPARs and an agonist activity is found, it is judged that the possibility of having a metabolism improving effect is high, or a metabolism improving effect is present. As one example, the PPAR reporter assay described in FEBS Letters 514 (2002) p. 315-322 can be performed. However, the method is not limited thereto.

Alternatively, oxo fatty acid and the like may be administered to obesity or diabetes animal model, body weight, organ weight, blood glucose level, neutral fats value, oxygen consumption level, rectal temperature and the like are measured, and the presence or absence of the changes thereof can be confirmed. The obesity or diabetes animal model is not limited as long as it is an animal showing the properties. For example, as the aforementioned animal model, commercially available KKAy mouse, NOD mouse, NSY mouse, TSOD mouse, ZDF/Crl-Leprfa rat, SDT/Jcl rat and the like can be recited. The body weight, organ weight, blood glucose level, neutral fats value, oxygen consumption level, rectal temperature and the like can be measured by a known method. Using these as indices, when a decrease in the body weight or organ weight, or blood glucose level, neutral fats value is observed, or when an increase in the oxygen consumption level or rectal temperature is observed, it is judged that the possibility of having a metabolism improving effect is high, or a metabolism improving effect is present.

Alternatively, as described in the below-mentioned Examples, whether a lipid synthesis-promoting action induced by LXR agonist is suppressed by the addition of oxo fatty acid and the like can be confirmed. As a method therefor, for example, Journal of Lipid Research 47 (2006) 2712-2717 can be referred to, but the method is not limited thereto. The method described in the aforementioned document includes adding a LXR agonist, and (1) measuring the expression level of mRNA and/or protein of lipid synthesis-related factors, for example, SREBP-1c, mature and immature SREBP-1, SCD-1, FAS, ACC1 and/or ACC2, (2) measuring an intracellular triacylglycerol level, or (3) performing luciferase assay using LXR responsive sequence. Examples of the LXR agonist include, but are not limited to, T0901317, 22(R)-hydroxycholesterol, 24(S)-hydroxycholesterol and the like. When the expression level and the like of mRNA and/or protein of lipid synthesis-related factor decreases, it is judged that the lipid synthesis is suppressed, and the possibility of having a metabolism improving effect is high, or a metabolism improving effect is present.

In the present invention, oxo fatty acid is an oxo fatty acid having 18 carbon atoms and a carbonyl group at the 10- or 12-position (hereinafter sometimes to be abbreviated as "10-oxo fatty acid" or "12-oxo fatty acid"). It further includes a carbonyl group at the 10-position and a cis double bond at the 12-position (hereinafter sometimes to be abbreviated as "10-oxo,cis-12 fatty acid"), an oxo fatty acid having 18 carbon atoms, a carbonyl group at the 10-position and a trans double bond at the 11-position (hereinafter sometimes to be abbreviated as "10-oxo,trans-11 fatty acid"), and an oxo fatty acid having 18 carbon atoms and a carbonyl group at the 10-position and not having a double bond at the 11- and 12-positions (hereinafter sometimes to be abbreviated as "10-oxo,11,12-saturated fatty acid").

More specifically, it includes 10-oxo-cis-12-octadecenoic acid (KetoA), 10-oxo-cis-12,cis-15-octadecadienoic acid (hereinafter to be also referred to as "αKetoA"), 10-oxo-cis-6,cis-12-octadecadienoic acid (hereinafter to be also referred to as "γKetoA"), 10-oxo-cis-6,cis-12,cis-15-octadecatrienoic acid (hereinafter to be also referred to as "sKetoA"), 10-oxooctadecanoic acid (hereinafter to be also referred to as "KetoB"), 10-oxo-cis-6-octadecenoic acid (hereinafter to be also referred to as "γKetoB"), 10-oxo-cis-15-octadecenoic acid (hereinafter to be also referred to as "αKetoB"), 10-oxo-cis-6,cis-15-octadecadienoic acid (hereinafter to be also referred to as "sKetoB"), 12-oxooctadecanoic acid (hereinafter to be also referred to as "rKetoB"), 10-oxo-trans-11-octadecenoic acid (hereinafter to be also referred to as "KetoC"), 10-oxo-cis-6,trans-11-octadecadienoic acid (hereinafter to be also referred to as "γKetoC"), 10-oxo-trans-11,cis-15-octadecadienoic acid (hereinafter to be also referred tows "αKetoC"), 10-oxo-cis-6,trans-11,cis-15-octadecatrienoic acid (hereinafter to be also referred to as "sKetoC"), 12-oxo-cis-9-octadecanoic acid (hereinafter to be also referred to as "KetoRA") and the like.

In the present invention, hydroxy fatty acid refers to a hydroxy fatty acid having 18 carbon atoms and a hydroxyl group at the 10-position (hereinafter sometimes to be abbreviated as "10-hydroxy fatty acid"), or a hydroxy fatty acid having 18 carbon atoms and a hydroxyl group at the 12-position (hereinafter sometimes to be abbreviated as "12-hydroxy fatty acid"). Here, a "10,12-dihydroxy fatty acid" having a hydroxyl group at the 10- and 12-positions is also encompassed as one embodiment of "10-hydroxy fatty acid", "12-hydroxy fatty acid". Furthermore, a hydroxy fatty acid having 18 carbon atoms, a hydroxy group at the 10-position and a cis double bond at the 12-position (hereinafter sometimes to be abbreviated as "10-hydroxy,cis-12 fatty acid"), a hydroxy fatty acid having 18 carbon atoms, a hydroxyl group at the 10-position and a trans double bond at the 11-position (hereinafter sometimes to be abbreviated as "10-hydroxy,trans-11 fatty acid"), and a hydroxy fatty acid having 18 carbon atoms and a hydroxyl group at the 10-position and free of a double bond at the 11 and 12-positions (hereinafter sometimes to be abbreviated as "10-hydroxy, 11,12-saturated fatty acid") are also encompassed.

More specific examples include, but are not limited to, 10-hydroxy-cis-12-octadecenoic acid (HYA), 10-hydroxy-cis-12,cis-15-octadecadienoic acid (hereinafter to be also referred to as "αHYA"), 10-hydroxy-cis-6,cis-12-octadecadienoic acid (hereinafter to be also referred to as "γHYA"), 10-hydroxy-cis-6,cis-12,cis-15-octadecatrienoic acid (hereinafter to be also referred to as "sHYA"), 10,12-dihydroxyoctadecanoic acid (hereinafter to be also referred to as "rHYA"), 10-hydroxyoctadecanoic acid (hereinafter to be also referred to as "HYB"), 10-hydroxy-cis-15-octadecenoic acid (hereinafter to be also referred to as "αHYB"), 10-hydroxy-cis-6-octadecenoic acid (hereinafter to be also referred to as "γHYB"), 10-hydroxy-cis-6,cis-15-octadecadienoic acid (hereinafter to be also referred to as "sHYB"), 12-hydroxyoctadecanoic acid (hereinafter to be also referred to as "rHYB"), ricinoleic acid (hereinafter to be also referred to as "RA"), 10-hydroxy-trans-11-octadecenoic acid (hereinafter to be also referred to as "HYC"), 10-hydroxy-trans-11,cis-15-octadecadienoic acid (hereinafter to be also referred to as "αHYC"), 10-hydroxy-cis-6,trans-11-octadecadienoic acid (hereinafter to be also referred to as "γHYC"), 10-hydroxy-cis-6,trans-11,cis-15-octadecatrienoic acid (hereinafter to be also referred to as "sHYC") and the like.

The rare fatty acids such as oxo fatty acid, hydroxy fatty acid and the like to be used in the present invention can be prepared by the method described in Japanese patent application No. 2012-108928, and HYA can be prepared by reference to Biochemical and Biophysical Research Communications 416 (2011) p. 188-193 and the like. As RA, rHYB and the like, commercially available products can be used. KetoRA, rKetoB can be prepared RA by utilizing the following chromic acid oxidation and the like.

The specific method described in Japanese patent application No. 2012-108928 is as follows.

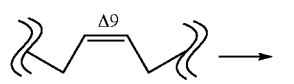

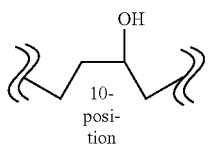

(reaction 1)

10-oxo fatty acid is produced from an unsaturated fatty acid having 18 carbon atoms and a cis double bond at the 9-position (hereinafter sometimes to be abbreviated as "cis-9 unsaturated fatty acid") by two-step reaction. In the first reaction (reaction 1), 10-hydroxy fatty acid is produced from cis-9 unsaturated fatty acid by a hydratase reaction.

The substrate in "reaction 1" is not particularly limited as long as it is an unsaturated fatty acid having 18 carbon atoms and a cis double bond at the 9-position, and examples thereof include monoeneoic acid (18:1), dienoic acid (18:2), trienoic acid (18:3), tetraenoic acid (18:4), pentaenoic acid (18:5) and the like. More preferred are dienoic acid, trienoic acid and tetraenoic acid, and particularly preferred are dienoic acids and trienoic acids. In the present specification, "fatty acid" encompasses not only free acids but also ester form, salt with basic compound and the like.

Examples of the monoenoic acid include oleic acid, ricinoleic acid and the like.

Examples of the dienoic acid include linoleic acid, cis-9, trans-11-octadecadienoic acid and the like.

Examples of the trienoic acids include α-linolenic acid, γ-linolenic acid and the like.

Examples of the tetraenoic acid include stearidonic acid and the like.

While hydratase that catalyzes reaction 1 is not particularly limited as long as it is an enzyme capable of utilizing the above-mentioned cis-9 unsaturated fatty acid as a substrate and capable of converting to 10-hydroxy fatty acid, for example, lactic acid bacteria-derived fatty acid-hydratase (CLA-HY) is preferable. More preferred is *Lactobacillus plantarum*-derived CLA-HY, and particularly preferred is *L. plantarum* FERM BP-10549 strain-derived CLA-HY. CLA-HY can be obtained by the method described in JP-A-2007-259712, or the like.

The amount of hydratase to be added is, for example, 0.001-0.10 mg/ml, preferably 0.1-5 mg/ml, more preferably 0.2-2 mg/ml.

A "cofactor" may be used for reaction 1 and, for example, NADH, NADPH, FADH$_2$ and the like can be used. The concentration of addition may be any as long as the hydration reaction proceeds efficiently. It is preferably 0.001-20 mM, more preferably 0.01-10 mM.

Furthermore, an "activator" may be used for the enzyme reaction and, for example, one or more compounds selected from the group consisting of potassium molybdate, disodium molybdate(VI) anhydrate, disodium molybdate(VI) dihydrate, sodium orthovanadate(V), sodium metavanadate (V), potassium tungstate(VI), sodium tungstate(VI) anhydrate and sodium tungstate(VI) dihydrate can be mentioned. The concentration of addition thereof may be any as long as the hydration reaction proceeds efficiently. It is preferably 0.1-20 mM, more preferably 1-10 mM.

For example, rHYA can be obtained by adding 100 mM potassium phosphate buffer (pH 6.5) containing hydration enzyme (wet bacteria body weight 0.7 g) expressed in *Escherichia coli*, NADH (33 mg), FAD (0.8 mg), ricinoleic acid (1 g), BSA (0.2 g) to RA to a total amount of 10 ml, and performing a shaking reaction anaerobically at 37° C. for 63 hr, 225 rpm.

On the other hand, 12-hydroxy fatty acid can be obtained, for example, by hydrolysis of natural oil containing, as a main component, triglyceride ester containing 12-hydroxy fatty acid as a constituent fatty acid. For example, RA can be obtained by hydrolysis of castor oil, and rHYB can be obtained by hydrolysis of hydrogenated castor oil.

(reaction 2)

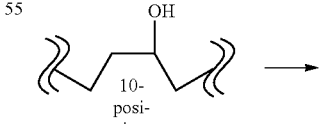

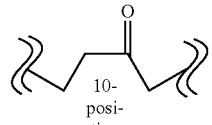

In the second reaction (reaction 2), 10-oxo fatty acid is produced from 10-hydroxy fatty acid by a dehydrogenase reaction or chemical oxidation using chromic acid.

While the dehydrogenase that catalyzes reaction 2 is not particularly limited as long as it is an enzyme capable of utilizing 10-hydroxy fatty acid as a substrate and capable of converting to 10-oxo fatty acid, for example, lactic acid bacteria-derived hydroxy fatty acid-dehydrogenase (CLA-DH) is preferable. More preferred is *Lactobacillus plantarum*-derived CLA-DH, and particularly preferred is *L. plantarum* FERM BP-10549 strain-derived CLA-DH. CLA-DH can be obtained by the method described in JP-A-2007-259712, or the like.

The amount of dehydrogenase to be added is, for example, 0.001-10 mg/ml, preferably 0.1-5 mg/ml, more preferably 0.2-2 mg/ml.

A "cofactor" may be used for reaction 2 and, for example, NAD, NADP, FAD and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

The second reaction can be performed by chemical oxidation.

As the chemical oxidation, methods known per se, for example, chromic acid oxidation, preferably Jones oxidation and the like can be mentioned. As the chromic acid, salts and complexes of the compound such as anhydrous chromic acid $CrO_3$, chromic acid $H_2CrO_4$ and dichromic acid $H_2Cr_2O_7$ can be used.

Similarly, 12-oxo fatty acid can be obtained from 12-hydroxy fatty acid. For example, KetoRA can be obtained by the following method.

To be specific, sulfuric acid (2.3 ml) and water (7.7 ml) are added to anhydrous chromic acid (2.67 g), and acetone (90 ml) is added to the mixture to give a chromic acid solution. 5 g of RA and 100 ml of acetone are added in an Erlenmeyer flask, and the above-mentioned chromic acid solution is added by one drop while stirring in a stirrer on ice. When the solution turns from blue green into pale orange, dropwise addition of the chromic acid solution is stopped, the reaction is discontinued with isopropyl alcohol. The precipitated sediment is removed by centrifugation, and the obtained centrifuged supernatant is placed in a separating funnel and blended well with hexane (100 ml) and Milli-Q water (100 ml). The hexane layer is recovered by centrifugation, washed several times with Milli-Q water, and concentrated by a rotary evaporator to extract the reaction product and unreacted substrates. About 98% of the extract can be confirmed to be KetoRA. Silica gel (Wakogel(r)C-100) in a 20- to 30-fold weight that of the extract (mixture containing KetoRA) is swollen with hexane, packed in a glass column, and sodium sulfate (anhydrous) is placed thereon. The extract obtained above (mixture containing KetoRA) is suspended in hexane:diethyl ether=8:2 eluent and applied to the column. The eluent is flown at a flow rate of about 2 ml and the solution discharged from the column is fractionated and recovered. The recovered each fraction is analyzed by LC/MS and gas chromatographys. The fractions containing only KetoRA are collected and concentrated by a rotary evaporator to give KetoRA having purity of not less than 99%.

Also, rKetoB can be obtained by chromic acid oxidation in the same manner as in rHYB.

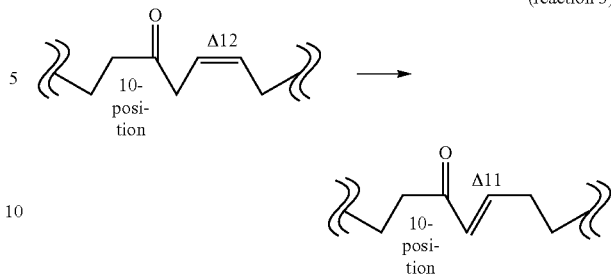
(reaction 3)

10-oxo,trans-11 fatty acid is produced from an oxo fatty acid having 18 carbon atoms, a carbonyl group at the 10-position and a cis double bond at the 12-position by an isomerase reaction (reaction 3).

The "substrate" of reaction 3 is not particularly limited as long as it is 10-oxo,cis-12 fatty acid induced from an unsaturated fatty acid having 18 carbon atoms and a cis double bond at the 9- and 12-positions, by the above-mentioned reactions 1 and 2. Examples thereof include KetoA induced from linoleic acid, αKetoA induced from α-linolenic acid, γKetoA induced from γ-linolenic acid, sKetoA induced from stearidonic acid and the like. The substrate may be obtained by a method other than reactions 1 and 2.

While isomerase that catalyzes reaction 3 is not particularly limited as long as it is an enzyme capable of utilizing the above-mentioned 10-oxo,cis-12 fatty acid as a substrate and capable of converting to 10-oxo,trans-11 fatty acid, for example, lactic acid bacteria-derived oxo fatty acid-isomerase (CLA-DC) is preferable. More preferred is *Lactobacillus plantarum*-derived CLA-DC, and particularly preferred is *L. plantarum* FERM BP-10549 strain-derived CLA-DC. CLA-DC can be obtained by the method described in JP-A-2007-259712, or the like.

The amount of isomerase to be added is, for example, 0.001-10 mg/ml, preferably 0.1-5 mg/ml, more preferably 0.2-2 mg/ml.

An "activator" may be used for the isomerase reaction and, for example, compounds similar to those recited as examples in the above-mentioned reaction 1 can be used at a similar addition concentration.

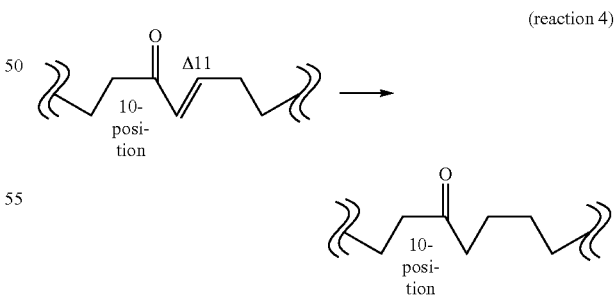
(reaction 4)

10-Oxo,11,12-saturated fatty acid is produced from an oxo fatty acid having 18 carbon atoms, a carbonyl group at the 10-position and a trans double bond at the 11-position (10-oxo,trans-11 fatty acid) by a saturase reaction (reaction 4).

The "substrate" of reaction 4 is not particularly limited as long as it is 10-oxo,trans-11 fatty acid produced by the above-mentioned reaction 3. Examples thereof include KetoC induced from KetoA, αKetoC induced from αKetoA, γKetoC induced from γKetoA, sKetoC induced from sKetoA and the like. The substrate may be obtained by a method other than reaction 3.

While saturase that catalyzes reaction 4 is not particularly limited as long as it is an enzyme capable of utilizing the above-mentioned 10-oxo,trans-11 fatty acid as a substrate and capable of converting to 10-oxo,11,12-saturated fatty acid, for example, oxo fatty acid-enone reductase (CLA-ER) derived from lactic acid bacteria is preferable. More preferred is *Lactobacillus plantarum*-derived CLA-ER, and particularly preferred is *L. plantarum* FERM BP-10549 strain-derived CLA-ER.

The above-mentioned enzyme "CLA-ER" is
(a) an enzyme protein consisting of the amino acid sequence shown in SEQ ID NO: 2,
(b) a protein comprising an amino acid sequence which is the amino acid sequence shown in SEQ ID NO: 2 wherein one or plural amino acids are deleted and/or substituted and/or inserted and/or added, and having an enzyme activity of catalyzing the above-mentioned reaction 4, or
(c) a protein encoded by a base sequence that hybridizes to a nucleic acid consisting of a complementary chain sequence of the base sequence shown in SEQ ID NO: 1 under stringent conditions, and having an enzyme activity to catalyze the above-mentioned reaction 4.

More specific examples of the above-mentioned (b) include a protein containing (i) an amino acid sequence which is the amino acid sequence shown in SEQ ID NO: 2, wherein 1-20, preferably 1-10, more preferably 1—several (5, 4, 3 or 2) amino acids are deleted, (ii) an amino acid sequence which is the amino acid sequence shown in SEQ ID NO: 2, wherein 1-20, preferably 1-10, more preferably 1—several number (5, 4, 3, or 2) amino acids are added, (iii) an amino acid sequence which is the amino acid sequence shown in SEQ ID NO: 2, wherein 1-20, preferably 1-10, more preferably 1—several (5, 4, 3 or 2) amino acids are inserted, (iv) an amino acid sequence which is the amino acid sequence shown in SEQ ID NO: 2, wherein 1-20, preferably 1-10, more preferably 1—several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysine and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

CLA-ER can be isolated from, for example, the fungus and culture medium of *L. plantarum* FERM BP-10549 strain by a protein separation and purification technique known per se, for example, by using the enzyme activity that catalyzes the above-mentioned reaction 4 as an index. Alternatively, it can also be produced by recombination by synthesizing the total base sequence of the coding region of CLA-ER based on the information of the base sequence shown in SEQ ID NO: 1, or designing a primer capable of amplifying CLA-ER gene segment so containing the coding region, performing PCR using cDNA or genome DNA prepared from the above-mentioned strain as a template, cloning the obtained amplification fragment to a suitable expression vector and introducing same into a host cell, and cultivating the cell.

As a vector containing a nucleic acid encoding the above-mentioned CLA-ER, one suitable for a host cell to be introduced with the vector may be appropriately selected according to the object (e.g., protein expression) and can be used. The expression vector can contain an appropriate promoter, a transcription termination signal, and a selection marker gene (drug resistance gene, gene that complements auxotrophic mutation etc.). Also, it may contain a sequence encoding a tag sequence useful for separation and purification of the expressed protein and the like. Alternatively, the vector may be incorporated into the genome of a target host cell. The vector can be introduced into a target host cell by a transformation method known per se such as a competent cell method, a protoplast method, a calcium phosphate coprecipitation method and the like.

The above-mentioned "host cell" may be any cell as long as it can express a vector containing a nucleic acid encoding the above-mentioned CLA-ER, and bacterium, yeast, fungi, higher eukaryotic cell and the like can be mentioned. Examples of the bacterium include gram-positive bacteria such as *bacillus, Streptomyces* and the like and gram negative bacteria such as *Escherichia coli* and the like. A recombinant cell introduced with a vector containing a nucleic acid encoding CLA-ER can be cultivated by a method known per se which is suitable for the host cell.

"Purification" of the above-mentioned CLA-ER can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The amount of saturase to be added is, for example, 0.001-10 mg/ml, preferably 0.1-5 mg/ml, more preferably 0.2-2 mg/ml.

A "cofactor" may be used for reaction 4 and, for example, NADH and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

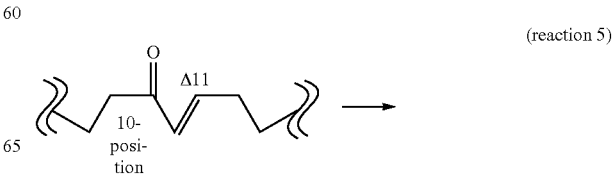

(reaction 5)

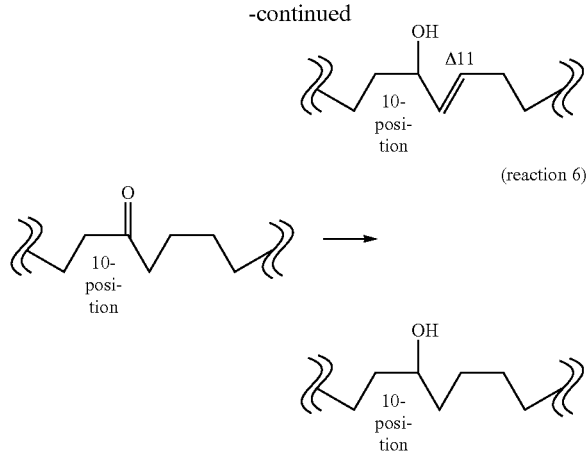

(reaction 6)

10-Hydroxy,trans-11 fatty acid is produced from an oxo fatty acid having 18 carbon atoms, a carbonyl group at the 10-position and a trans double bond at the 11-position (10-oxo,trans-11 fatty acid) by a dehydrogenase reaction (reaction 5) or 10-hydroxy,11,12-saturated fatty acid is produced from an oxo fatty acid having 18 carbon atoms and a carbonyl group at the 10-position and not having a double bond at the 11- and 12-positions (10-oxo,11,12-saturated fatty acid) by a dehydrogenase reaction (reaction 6).

The "substrate" of reaction 5 is not particularly limited as long as it is 10-oxo,trans-11 fatty acid produced by the above-mentioned reaction 3. Examples thereof include KetoC induced from KetoA, αKetoC induced from αKetoA, γKetoC induced from γKetoA, sKetoC induced from sKetoA and the like. The substrate may be obtained by a method other than reaction 3.

On the other hand, the "substrate" of reaction 6 is not particularly limited as long as it is 10-oxo,11,12-saturated fatty acid produced by the above-mentioned reaction 4. Examples thereof include KetoB induced from KetoC, αKetoB induced from αKetoC, γKetoB induced from γKetoC, sKetoB induced from sKetoC and the like. The substrate may be obtained by a method other than reaction 4.

While the dehydrogenase that catalyzes reaction 5 or reaction 6 is not particularly limited as long as it is an enzyme capable of utilizing 10-oxo,trans-11 fatty acid or 10-oxo,11,12-saturated fatty acid as a substrate and capable of converting to 10-hydroxy,trans-11 fatty acid or 10-hydroxy,11,12-saturated fatty acid, for example, lactic acid bacteria-derived hydroxy fatty acid-dehydrogenase (CLA-DH) is preferable. More preferred is Lactobacillus plantarum-derived CLA-DH, and particularly preferred is *L. plantarum* FERM BP-10549 strain-derived CLA-DH. While CLA-DH catalyzes the oxidation reaction in the above-mentioned reaction 2, it can also catalyze the reduction reaction in reaction 5 or reaction 6 as a reverse reaction.

The amount of dehydrogenase to be added is, for example, 0.001-10 mg/ml, preferably 0.1-5 mg/ml, more preferably 0.2-2 mg/ml.

A "cofactor" may be used for reaction 5 and reaction 6 and, for example, NADH, NADPH, FADH$_2$ and the like can be used. The concentration of addition may be any as long as the reduction reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

In the above-mentioned each reaction, the enzymes (hydratase, dehydrogenase, isomerase, saturating enzyme) are subjected to the reaction system in the form of recombinant cells (e.g., *Escherichia coli, Bacillus subtilis*, yeast, insect cell, animal cell etc.) introduced with an expression vector containing a nucleic acid encoding same. In this case, the reaction can also be performed by cultivating the cells in a liquid medium suitable for the culture of the cells and added with a substrate and, where necessary, a cofactor and an activator. In addition, any of the above-mentioned enzymes may be a purified one or a crudely purified one. Alternatively, hydratase may be expressed in fungus such as *Escherichia coli* and the like and the fungus itself may be used or culture medium thereof may be used. Furthermore, the enzyme may be of a free type, or immobilized by various carriers.

The metabolism improving agent of the present invention containing oxo fatty acid and the like can also be applied to the improvement of lifestyle-related diseases. The "lifestyle-related disease" is a disease group for which life habits such as eating habit, exercise habit, rest, smoking, drinking and the like are involved in the onset and progression thereof, and includes pathologies such as adult obesity, child obesity, nutrition ataxia, anorexia, gastric cancer, large intestine cancer, gout, hypertension, arteriosclerosis, nephrolithiasis, myocardial infarction, angina pectoris, gastric ulcer, kidney disease, osteoporosis, periodontitis, alcoholic hepatitis, cirrhosis, liver cancer, lung cancer, bronchitis, emphysema, periodontal disease, cerebral apoplexy, cerebral infarction, aneurysm, overwork death, insomnia and the like.

Moreover, the metabolism improving agent of the present invention can also be used for the prophylaxis or improvement of diabetes (type 1 diabetes, type 2 diabetes, pregnancy diabetes etc.), diabetic complications (arteriosclerotic to diseases, diabetic retinopathy, diabetic nephropathy, diabetic neuropathy etc.), lipid metabolism abnormality, hyperlipidemia, hypercholesterolemia, hypertriglyceridemia, insulin resistance, and fatty liver.

Alternatively, the metabolism improving agent of the present invention can be used for the prophylaxis or treatment of at least one kind selected from the group consisting of obesity, diabetes, lipid metabolism abnormality, hyperlipidemia, hypercholesterolemia, hypertriglyceridemia, insulin resistance and fatty liver, by administration to human, or an animal other than human (e.g., dog, cat, mouse, rat, hamster, guinea pig, rabbit, swine, bovine, chicken, parakeet, hill myna, goat, horse, sheep, monkey etc.).

The metabolism improving agent of the present invention containing oxo fatty acid and the like can be used as, for example, a pharmaceutical product, a food, a feed, a cosmetic and the like, or by adding the agent to them.

The dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method. Since oxo fatty acid and the like are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the metabolism improving agent of the present invention is used as a food or a food additive, the form of the food is not particularly limited as long as it permits oral ingestion, such as solution, suspension, powder, solid formed article and the like. Specific examples include supplements (powder, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk beverage, coffee drinks, tea drinks, powder drinks, concentrated drinks, nutrition drinks, alcohol drinks etc.), confectionery (gummy candy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

When the metabolism improving agent of the present invention is used as a feed or a feed additive, the feed is, for example, pet food, stock raising or aquaculture feed additive and the like.

When the metabolism improving agent of the present invention is used as a cosmetic or a cosmetic additive, the cosmetic is, for example, cream, gel, skin milk, serum, toner, microemulsion essence, facial mask, foundation, lip rouge, eye shadow, shampoo, conditioner, bath additive and the like, and a flavor and the like may be mixed therewith.

Only one kind of oxo fatty acid and the like may be blended with the pharmaceutical product, food, feed, cosmetic and the like of the present invention or two or more kinds thereof may be used in combination.

The dose of the pharmaceutical product of the present invention or the ingestion amount of the food of the present invention can be appropriately determined according to the age and body weight of the patients or those who ingest same, symptom, administration time, dosage form, administration method, combination of medicaments and the like. For example, when the phalmaceutical product of the present invention is orally administered, the total amount of the oxo fatty acid and the like as an active ingredient is 0.02-100 mg/kg body weight, preferably 0.2-50 mg/kg body weight, per day for an adult, or 0.002 mg-50 mg/kg body weight, preferably 0.02-5.0 mg/kg body weight, by parenteral administration, which can be administered once a day or in several (2-5) portions per day. When it is ingested as a food, it can be added to a food such that the total ingestion amount of the oxo fatty acid and the like as an active ingredient is 1-6000 mg, preferably 10-3000 mg, per day for an adult. The ingestion amount of the feed of the present invention and the amount of use of the cosmetic of the present invention can each appropriately determined according to the above-mentioned ingestion amount of the food and the above-mentioned dose of the pharmaceutical product.

The present invention is explained in more detail in the following by referring to Examples. The Examples are mere exemplifications of the present invention and do not limit the scope of the present invention in any manner.

EXAMPLES

The rare fatty acids such as KetoA, HYA, γHYA, γKetoA, rHYA and the like used in the present invention were prepared based on the above-mentioned method (the method described in Japanese patent application No. 2012-108928). KetoRA was prepared from ricinoleic acid (RA) based on the above-mentioned method. GW7647 (PPARα agonist), Troglitazone (PPARγ agonist) were purchased from Sigma-Aldrich, T0901317 (LXR agonist) was purchased from Cayman Chemical, RA was purchased from NU-CHEK PREP, INC. (USA) (product number: U-50-A), EPA was purchased from NU-CHEK PREP, INC. (USA) (product number: U-99-A), LA was purchased from Sigma-Aldrich (product number: L1376), and other reagents were purchased from Wako Pure Chemical Industries, Ltd. or Nacalai Tesque and the like.

Example 1

Measurement of PPARα, γ Ligand Activity

To evaluate the function of oxo fatty acid and the like, PPARα, γ-activating action was measured first. The measurement was performed in reference to Nobuyuki Takahashi et al., FEES Letters 514 (2002) p. 315-322, "Dual action of isoprenols from herbal medicines on both PPAR-gamma and PPARalpha in 3T3-L1 adipocytes and HepG2 hepatocytes.", the section of Materials and Methods "Reporter plasmids and luciferase assays". To be specific, a plasmid containing DNA encoding a fused protein of PPARα, γ ligand binding region and GAL4 DNA binding region (pM-hPPARα or pM-hPPARγ), a reporter plasmid containing GAL4 binding DNA sequence linked to luciferase (p4xUASg-tk-luc), and internal control (pRL-CMV) to standardize transfection efficiency were introduced into CV-1 cell derived from the kidney of African green monkey. The ligand described below was added to the cells and, after incubation for 24 hr, luciferase activity was measured. As a ligand, KetoA and HYA were each added at 30 μM.

The concentration of the sample was adjusted with ethanol. Ethanol was used as a negative control, PPARα was used as a positive control, and GW7647 (10 nM) and Troglitazone (5 μM) were used as γ agonists. The results are shown in FIG. 1.

From FIG. 1, strong PPARα and γ agonist activity was found in KetoA, and PPARα agonist activity and some PPARγ agonist activity were found in HYA.

By a similar method, luciferase activity was also measured for αKetoA, γKetoA, sKetoA, KetoB, γKetoB, αKetoB, sKetoB, rKetoB, KetoC, γKetoC, αKetoC, sKetoC, KetoRA, αHYA, γHYA, sHYA, rHYA, HYB, αHYB, γHYB, sHYB, rHYB, RA, HYC, αHYC, γHYC and sHYC. As a result, KetoC, αKetoC, KetoRA and γKetoC showed PPARα and γ agonist activity, HYB, KetoB, αHYA, γHYA, rHYB, RA, rKetoB and rHYA showed PPARα agonist activity, and αKetoA and γKetoA showed PPARγ agonist activity.

Example 2

Effect in Obesity or Diabetes Model Mouse (1) Using KKAy mouse as obesity or diabetes model mouse, the effect of KetoA, HYA was evaluated. KKAy mice (KKAy/TaJcl, male, 4-week-old, purchased from CLEA Japan, Inc. and individually bred) were preliminarily bred on a commercially available normal diet (ND) for 1 week, divided into 5 groups, and each group was bred on a high-fat diet (HFD) as a basic feed and given a non-addition feed (control group), or a feed added with different amounts of KetoA and HYA for 4 weeks. The KetoA, HYA-added feed was prepared by adding KetoA, HYA to HFD such that the amount to be added was 0.05% (w/w) (0.05% group) or 0.1% (w/w) (0.1% group).

(2) The profile of the body weight and blood glucose level of the KKAy mouse was measured. After the start of the test feed breeding, the oxygen consumption level was measured on day 16-19, an oral glucose loading test was performed on day 24, and the rectal temperature was measured on day 26. The next day of the completion of experimental breeding, the KKAy mouse was dissected, and the organ weight and plasma neutral fat level were measured.

Figure 2:
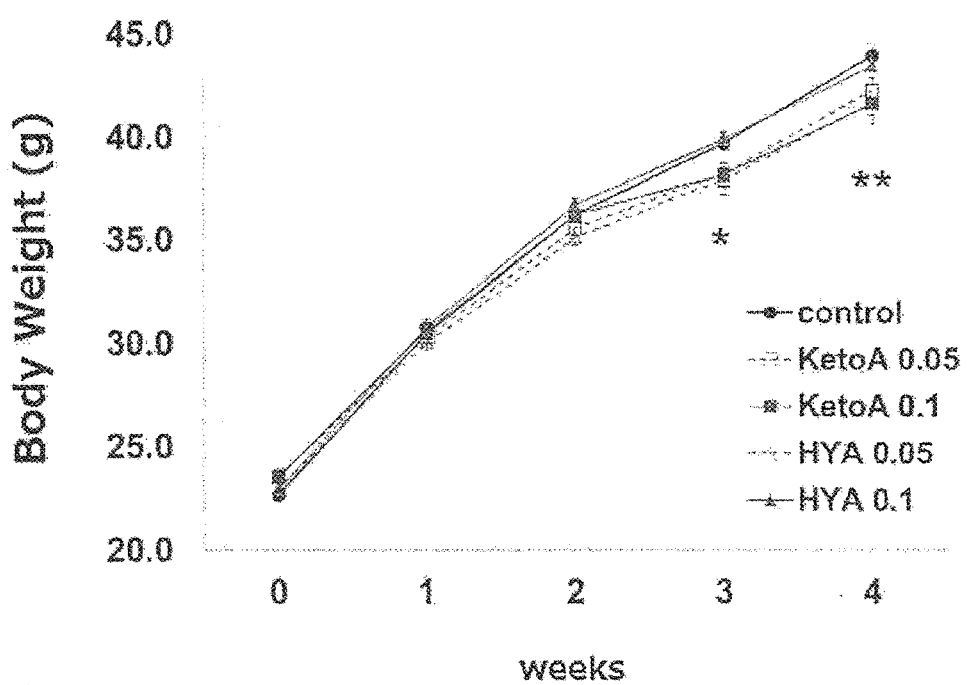
FIG. 2 shows changes in the body weight of mouse after feeding KetoA or HYA, wherein the vertical axis shows body weight (g), and the horizontal axis shows period (weeks) lapsed.

(3) The profile of the body weight of KKAy mouse is shown in FIG. 2. In the KetoA-added feed group, a body weight increase suppression tendency was found in the 0.05% group, and significant suppression of body weight increase was found in the 0.1% group. In the HYA-added feed group, significant suppression of body weight increase was found in the 0.05% group. In the Figure, * shows $P<0.05$, and ** shows $P<0.01$ (hereinafter the same for FIGS. 3-7).

Figure 3:
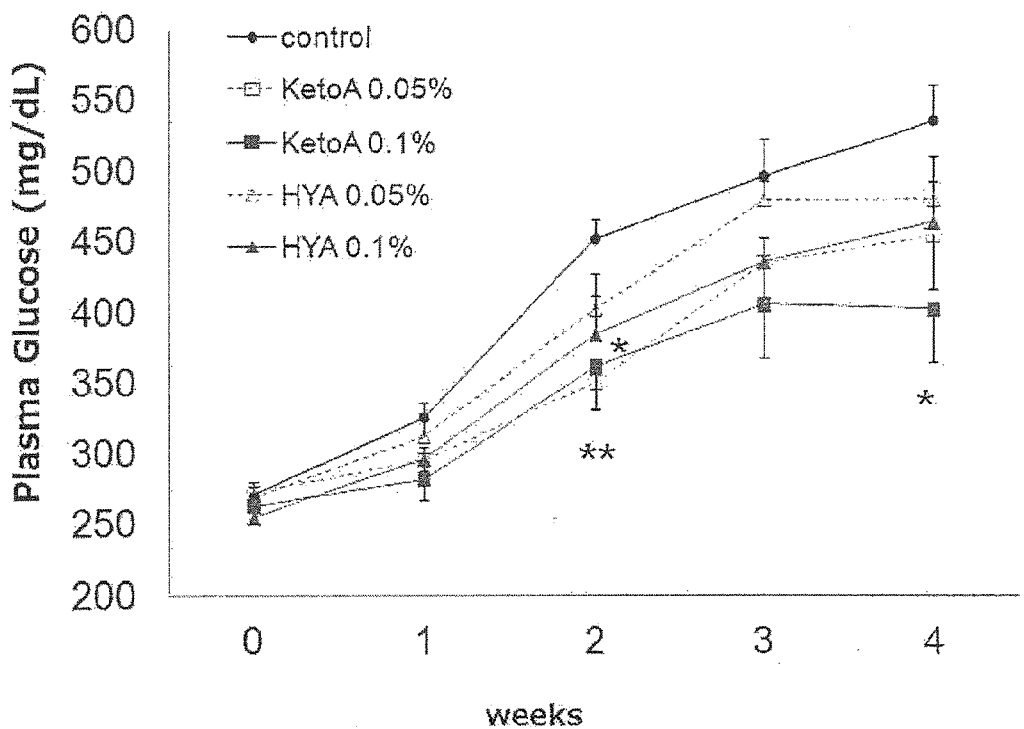
FIG. 3 shows changes in the blood glucose level of mouse after feeding KetoA or HYA, wherein the vertical axis shows plasma glucose concentration (mg/dL), and the horizontal axis shows period (weeks) lapsed.
Figure 4:
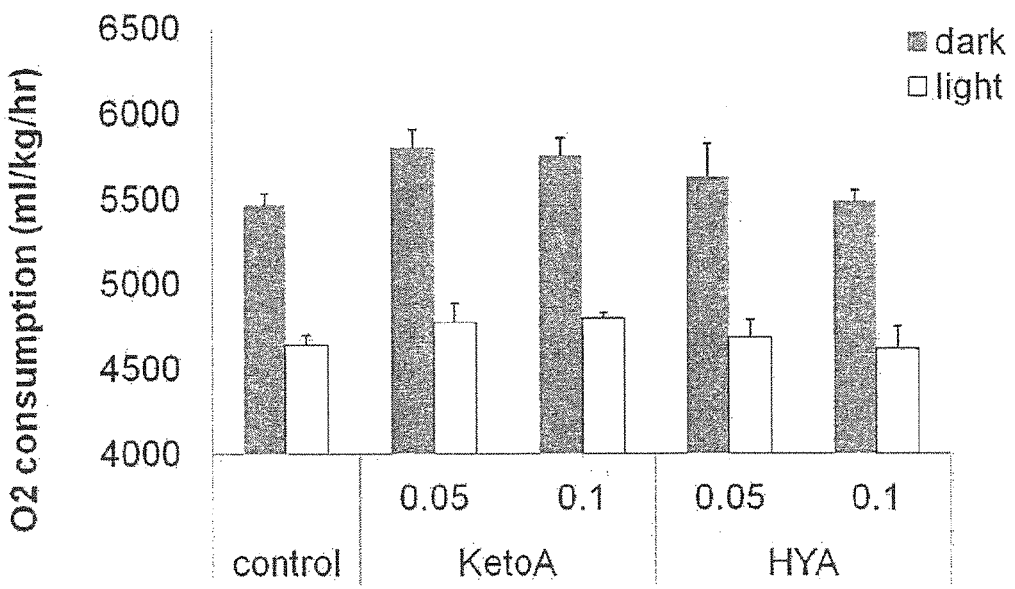
FIG. 4 shows oxygen consumption of mouse after feeding KetoA or HYA, wherein the vertical axis shows oxygen consumption amount (mL/kg/hr), dark shows measured value of dark period, and light shows the measured value of light period.
Figure 5:
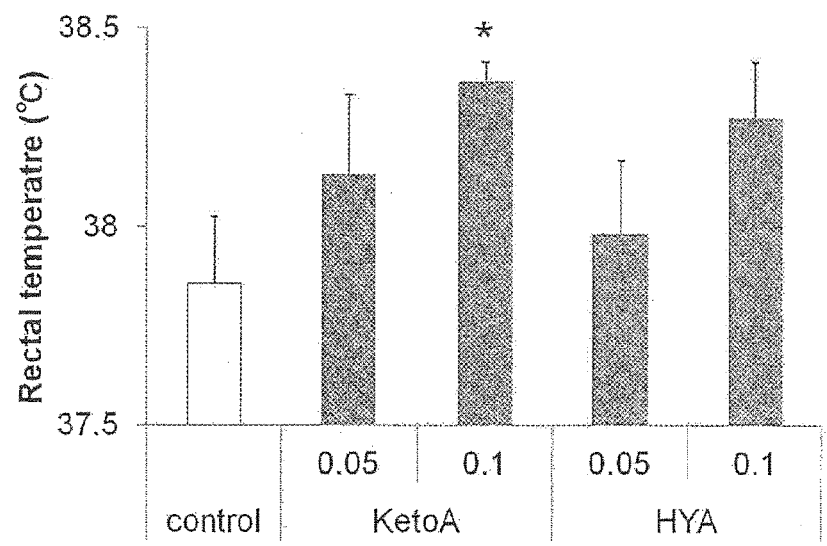
FIG. 5 shows rectal temperature after feeding mouse with KetoA or HYA, wherein the vertical axis shows rectal temperature (° C.).
Figure 6:
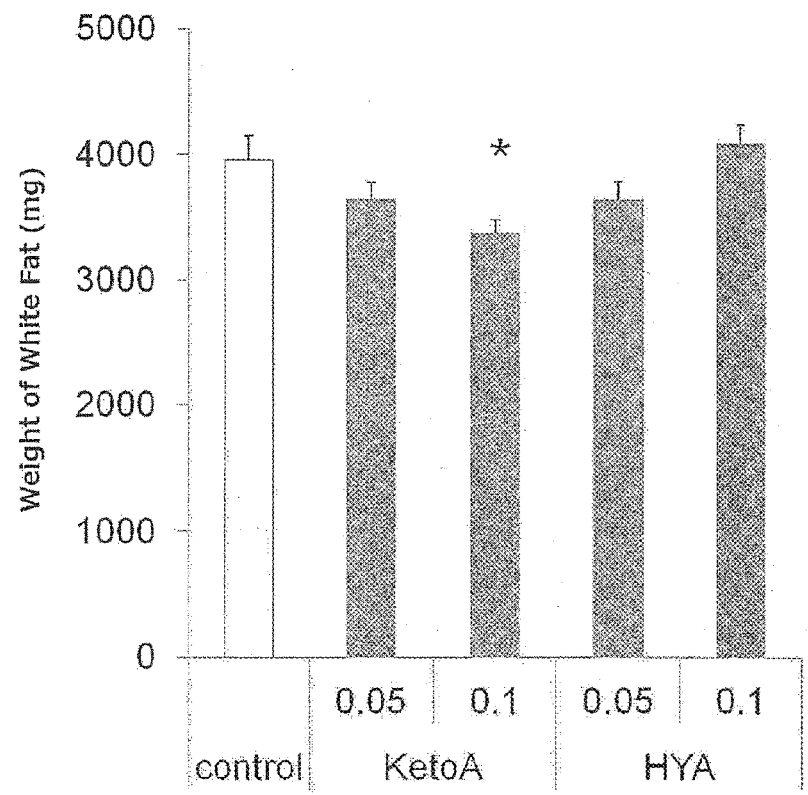
FIG. 6 shows white fat weight after feeding mouse with KetoA or HYA, wherein the vertical axis shows intraperitoneal white fat weight (mg).
Figure 7:
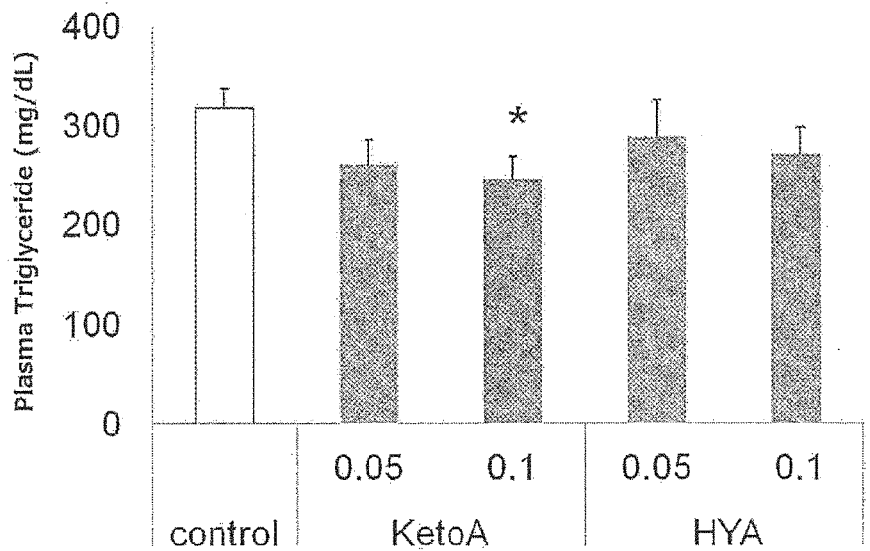
FIG. 7 shows neutral fats after feeding mouse with KetoA or HYA, wherein the vertical axis shows plasma triglyceride concentration (mg/dL).

The profile of the blood glucose level of KKAy mouse is shown in FIG. 3. At 4 weeks of the test diet ingestion, a tendency toward suppression of blood glucose increase was found in the 0.05% KetoA group as compared to the control group. Furthermore, a stronger, significant hypoglycemic action was found in the 0.1% KetoA group. On the other hand, the HYA group showed a tendency toward suppression of blood glucose level increase even though a significant difference was not found. The oxygen consumption level of the KKAy mouse is shown in FIG. 4. In addition, the results of rectal temperature of KKAy mouse are shown in FIG. 5. As compared to the control group, an increase in the oxygen consumption level was found in the KetoA group, and an increase in the rectal temperature was also found. The results show that heat generation is promoted in the KetoA group. The results of the organ weight (intraperitoneal white fat weight) of the KKAy mouse are shown in FIG. 6, and the results of plasma neutral fats are shown in FIG. 7. A significant decrease in both the intraperitoneal white fat weight and plasma neutral fat level was confirmed in the 0.1% KetoA group.

(4) From the above results, metabolism abnormality associated with obesity was improved in the KetoA ingestion group. Since an increase in the oxygen consumption level and elevation of rectal temperature were found, promoted heat generation is considered to contribute to the improvement of metabolism abnormality by KetoA.

Example 3

Effect on Induction of Fatty Acid Synthesis by LXR Agonist

Using human liver cancer-derived HepG2 cells (cell No.; JCRB1054, the Health Science Research Resources Bank), a suppressive effect on fatty acid synthesis promotion induced by LXR agonist was evaluated by reference to the method of Zaima et al. (Journal of Lipid Research 47, 2712-2717, 2006).

HepG2 cells ($2.0 \times 10^5$ cells/mL) were cultured in DMEM medium containing 10% FES for 24 hr, and the medium was exchanged with 0.1% BSA-containing DMEM medium containing 10 nM LXR agonist T0901317 (Cayman Chemicals) and 60 μM various fatty acid. After culture for 24 hr, the cells were recovered, and total RNA was extracted using Sepasol reagent (Nacalai Tesque). After DNase treatment, reverse transcription was performed using SuperScriptII (Invitrogen) to give a cDNA solution. Using SYBR Green Mix (Bio-Rad, Richmond, Calif.) and gene-specific primer (Table 1), real-time PCR was performed as follows.

TABLE 1

| mRNA | base sequence of primer | | reference |
|---|---|---|---|
| SREBP-1c | 5'-GGAGGGGTAGGGCCAACGGCCT-3' | (SEQ ID NO: 3) | Field et al., 2002* |
| | 5'-CATGTCTTCGAAAGTGCAATCC-3' | (SEQ ID NO: 4) | |
| SCD-1 | 5'-TGGTTTCACTTGGAGCTGTG-3' | (SEQ ID NO: 5) | NM_005063 |
| | 5'-GGCCTTGGAGACTTTCTTCC-3' | (SEQ ID NO: 6) | |
| FAS | 5'-ACAGGGACAACCTGGAGTTCT-3' | (SEQ ID NO: 7) | Field et al., 2002 |
| | 5'-CTGTGGTCCCACTTGATGAGT-3' | (SEQ ID NO: 8) | |
| ACC1 | 5'-ATCCCGTACCTTCTTCTACTG-3' | (SEQ ID NO: 9) | NM_198834 |
| | 5'-CCCAAACATAAGCCTTCACTG-3' | (SEQ ID NO: 10) | |
| ACC2 | 5'-CTCTGACCATGTTCGTTCTC-3' | (SEQ ID NO: 11) | NM_001093 |
| | 5'-ATCTTCATCACCTCCATCTC-3' | (SEQ ID NO: 12) | |

TABLE 1-continued

| mRNA | base sequence of primer | reference |
|---|---|---|
| 18S | 5'-TAAGTCCCTGCCCTTTGTACACA-3' (SEQ ID NO: 13)<br>5'-GATCCGAGGGCCTCACTAAAC-3' (SEQ ID NO: 14) | Field et al., 2002 |

*Field et al., 2002; Biochem J. 368: 855-864

1. Reaction at 96° C., 15 min, 2. reaction at 96° C., 15 sec, 3. reaction at 60° C. for 30 sec, 4. measurement of fluorescence, 5. 2-4 were repeated 40 times, 6. the melting curve was measured from 65° C. to 95° C. at 0.4° C. intervals. As the internal standard, 18S rRNA was used. The genes involved in the fatty acid synthesis as measured were Sterol regulatory element binding protein-1c (SREBP-1c), Stearoyl coenzyme A desaturase-1 (SCD-1), Fatty acid synthase (FAS), and Acetyl CoA carboxylase-1 and -2 (ACC-1, 2). As for the amount of accumulated intracellular TG, the lipid was extracted with chloroform-methanol, and quantified by triglyceride-'E Test Wako (Wako Pure Chemical Industries, Ltd.).

In addition, the protein expression level of immature and mature SREBP-1c was measured. Cells treated as mentioned above were dispersed in buffer A (250 mM sucrose, 10 mM HEPES-KOH, 10 mM KCl, 1.5 mM $MgCl_2$, 1 mM EDTA-Na, 1 mM EGTA-Na, pH 7.6) containing a protease inhibitor, passed 20 times through a 23 gauge injection needle, and centrifuged (1,000×g, 4° C., 5 min) to separate into supernatant 1 and precipitate 1. The precipitate 1 was re-dissolved in buffer B (20 mM HEPES-KOH, 0.42 M NaCl, 2.5% glycerol, 1.5 mM $MgCl_2$, 1 mM EDTA-Na, 1 mM EGTA-Na, pH 7.6), and centrifuged ($10^5$×g, 4° C., 15 min). The obtained supernatant 2 was used as a nuclear fraction (including mature form). The supernatant 1 was further centrifuged ($10^5$×g, 4° C., 15 min), and the obtained precipitate 2 was dissolved in cell lysate (10 mM Tris-HCl, 100 mM NaCl, 1% SDS, 1 mM EDTA-Na, 1 mM EGTA-Na) and used as a membrane fraction (including immature form). Using these as samples, measurement was performed by Western blot method using anti-SREBP-1 polyclonal antibody (Santa Cruz). Using Dual luciferase system (Promega), antagonizing action on LXR was evaluated by luciferase assay. p3xIR1-tk-Luc, pCMX-hLXRa, pRL-CMX were introduced into HepG2 cell. After culture in a 0.1% BSA-containing serum-free medium containing various fatty acids and T0901317 for 24 hr, the luciferase activity was measured.

Figure 8:
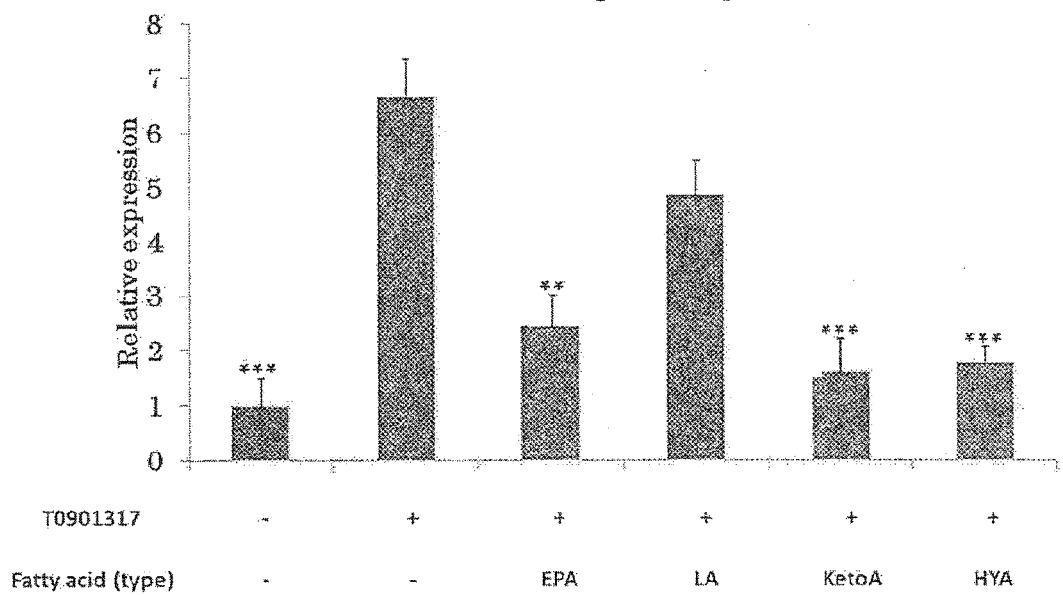
FIG. 8 shows an influence of KetoA or HYA on SREBP-1c mRNA expression induced by LXR agonist, wherein the vertical axis shows relative expression of SREBP-1c mRNA.
Figure 9:
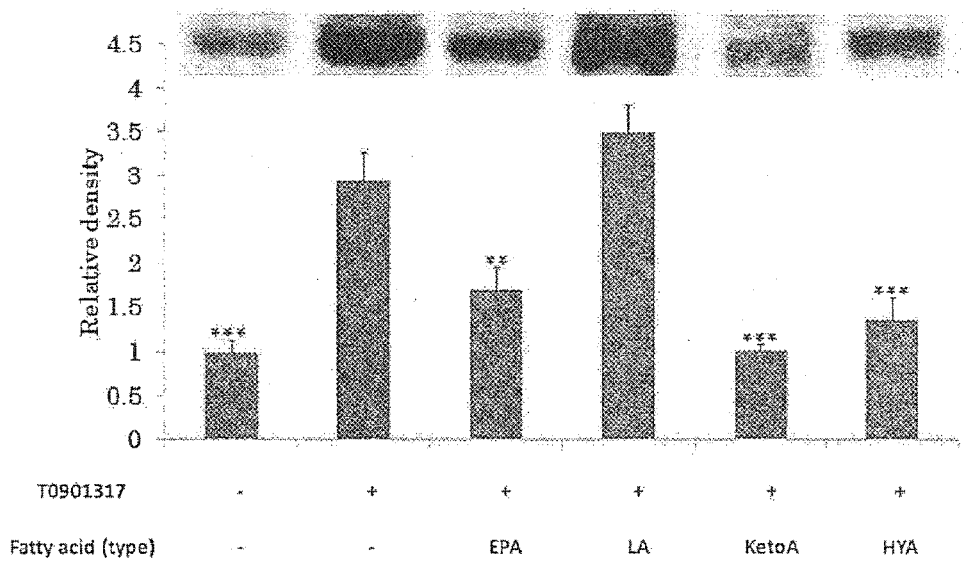
FIG. 9 shows an influence of KetoA or HYA on immature SREBP-1 expression induced by LXR agonist, wherein the vertical axis shows relative expression of immature SREBP-1c, and the upper graph shows Western blotting images.
Figure 10:
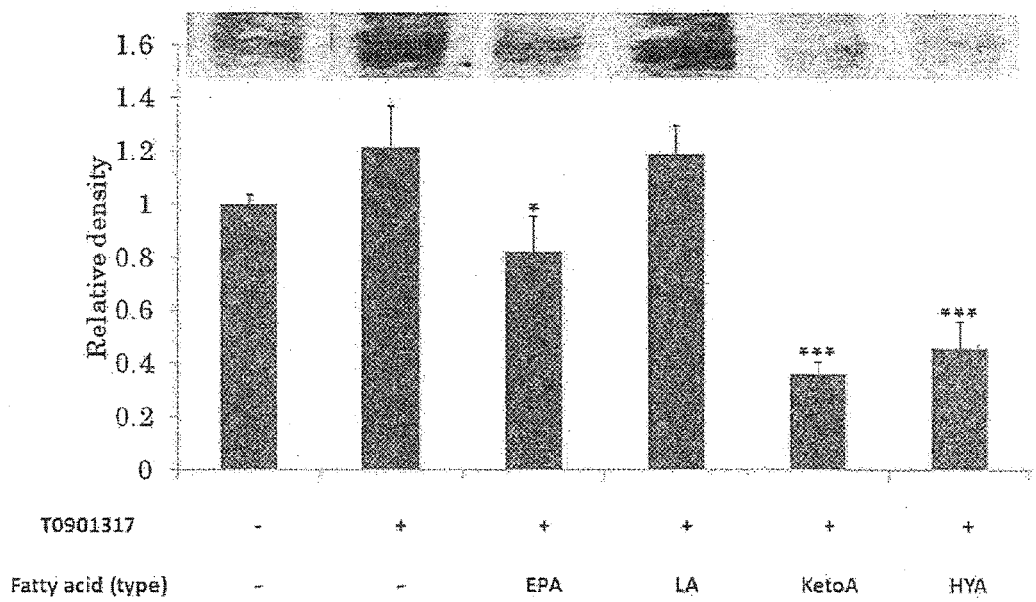
FIG. 10 shows an influence of KetoA or HYA on mature SREBP-1 expression induced by LXR agonist, wherein the vertical axis shows relative expression of mature SREBP-1c, and the upper graph shows Western blotting images.
Figure 11:
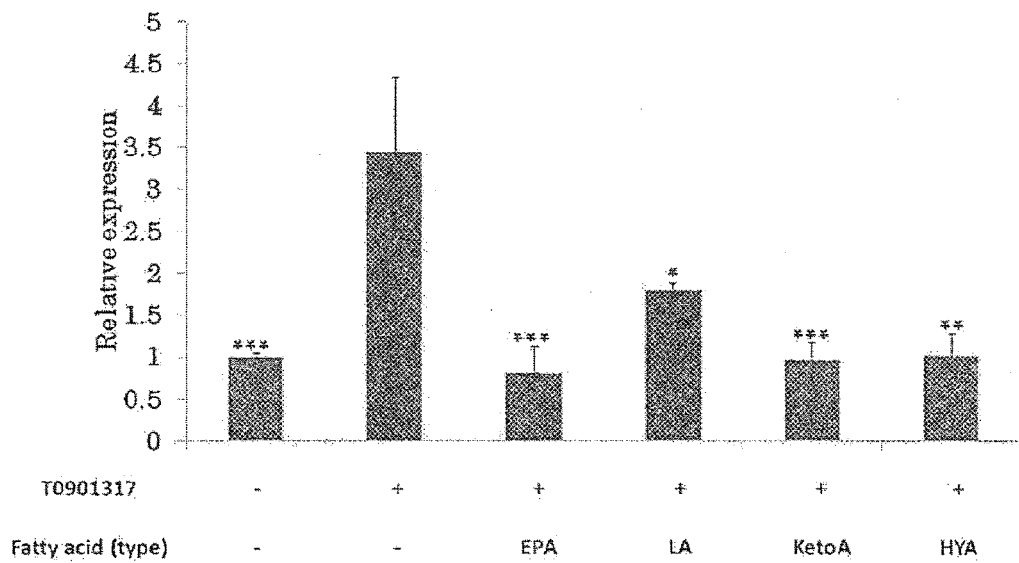
FIG. 11 shows an influence of KetoA or HYA on SCD-1 mRNA expression induced by LXR agonist, wherein the vertical axis shows relative expression of SCD-1 mRNA.
Figure 12:
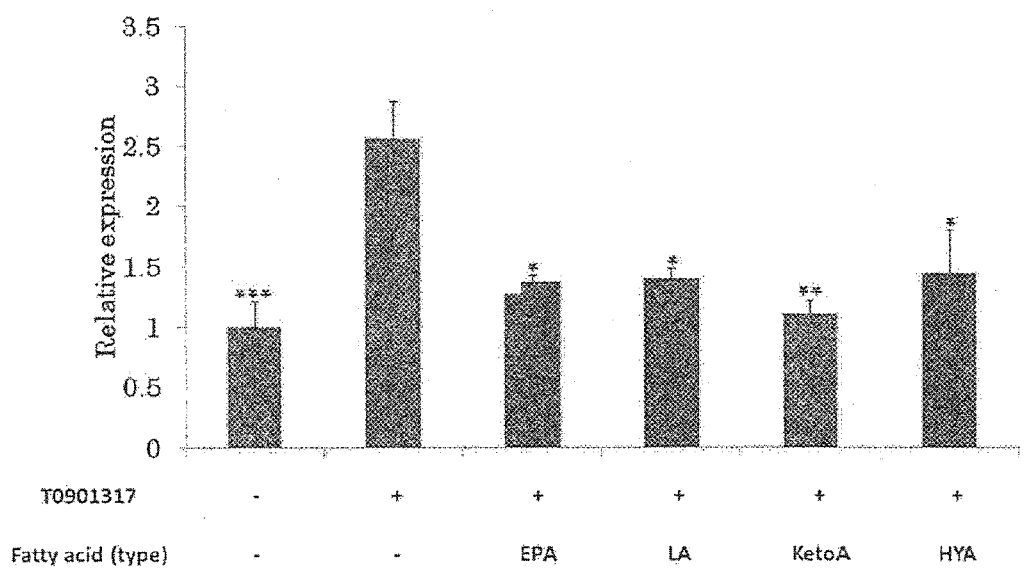
FIG. 12 shows an influence of KetoA or HYA on FAS mRNA expression induced by LXR agonist, wherein the vertical axis shows relative expression of FAS mRNA.
Figure 13:
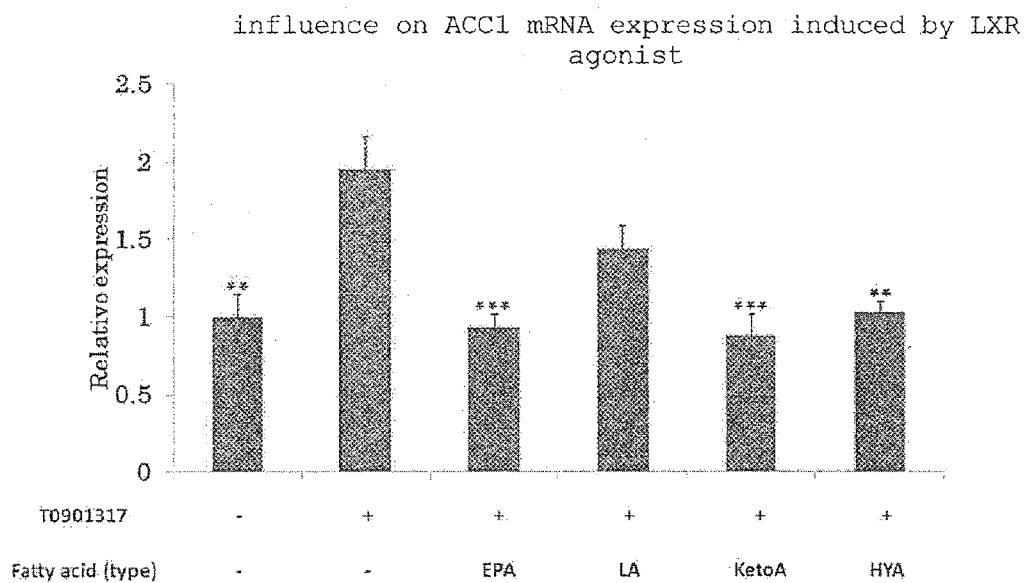
FIG. 13 shows an influence of KetoA or HYA on ACC1 mRNA expression induced by LXR agonist, wherein the vertical axis shows relative expression of ACC1 mRNA.
Figure 14:
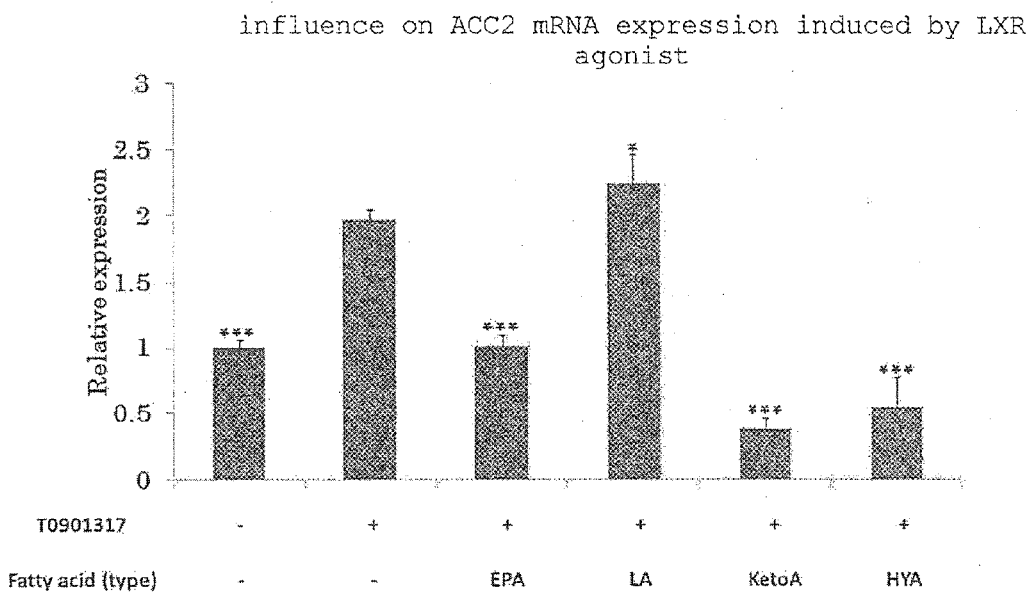
FIG. 14 shows an influence of KetoA or HYA on ACC2 mRNA expression induced by LXR agonist, wherein the vertical axis shows relative expression of ACC2 mRNA.
Figure 15:
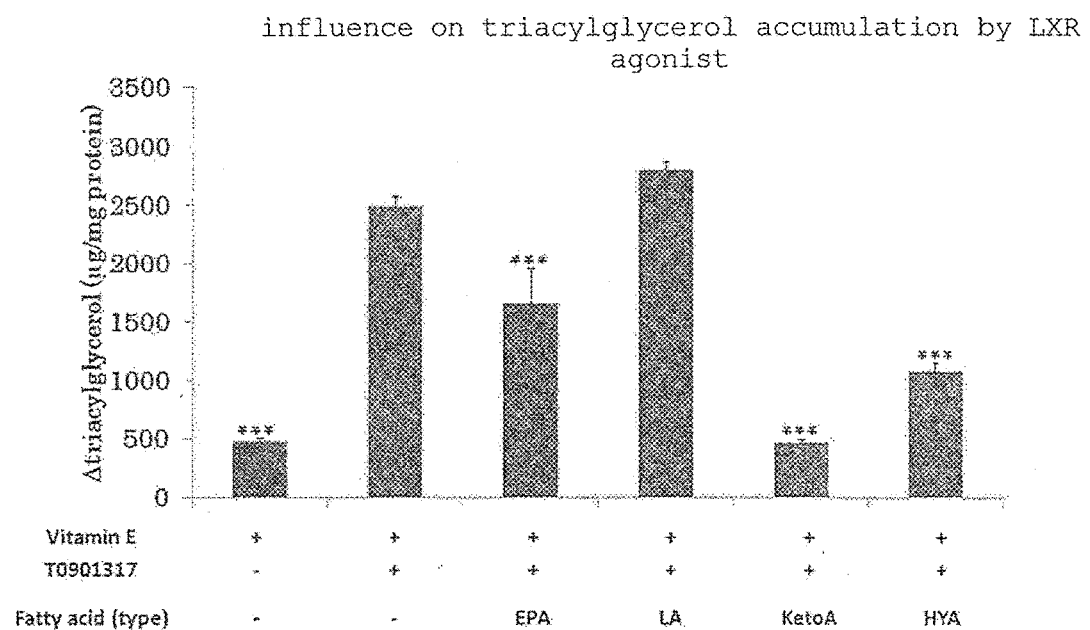
FIG. 15 shows an influence of KetoA or HYA on triacylglycerol accumulation by LXR agonist, wherein the vertical axis shows triacylglycerol level (μg/mg protein).
Figure 16:
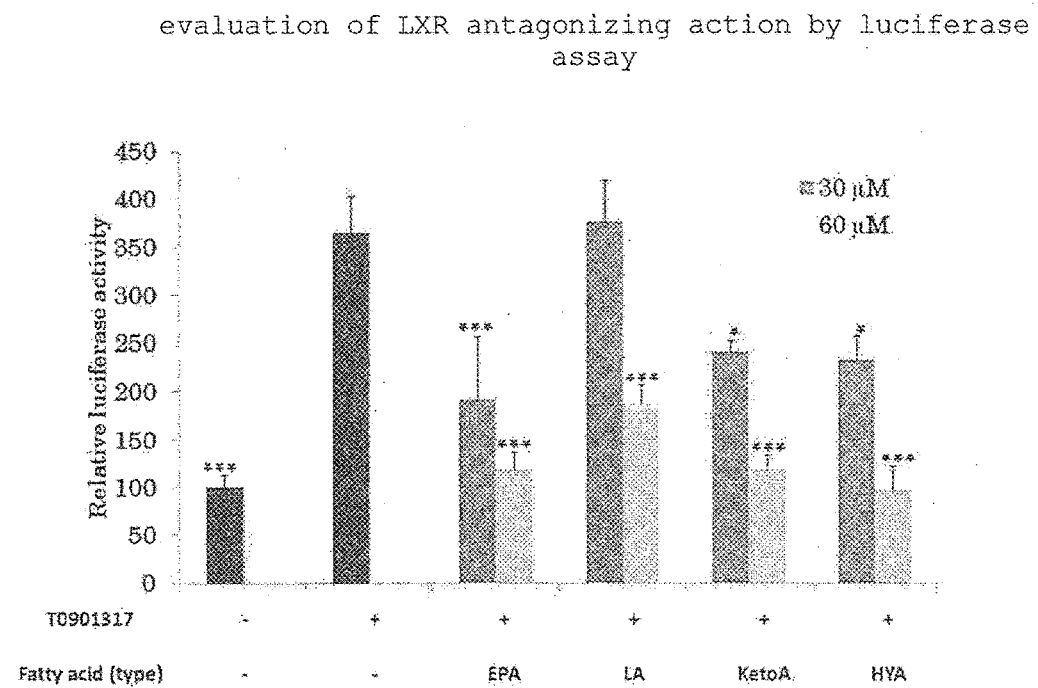
FIG. 16 shows evaluation of antagonizing action on LXR by luciferase assay, wherein the vertical axis shows relative luciferase activity.

FIG. 8 shows variation of expression of SREBP-1c mRNA. T0901317 increased the expression to about 7-fold, but a strong suppressive action was found in HYA and KetoA. The results of Western blotting also show that HYA and KetoA strongly suppressed promotion of the expression of mature and immature SREBP-1 induced by T0901317 (FIGS. 9, 10). It was also shown that lipid synthesis-related genes (SCD-1, FAS, ACC1, 2) under transcriptional regulation by SREBP-1c also show down regulation by these fatty acids (FIGS. 11-14). While the intracellular triacylglycerol level also increased by T0901317 (FIG. 15), the increase was significantly suppressed by the co-presence of these fatty acids. An antagonizing action on nuclear receptor LXR that regulates SREBP-1c was examined by luciferase assay to find that these fatty acids significantly suppress the action of T0901317, thus antagonizing LXR (FIG. 16).

In FIGS. 8-16, * shows $P<0.05$,  shows $P<0.001$, * shows $P<0.0001$ (vs. T0901317 addition, fatty acid non-addition).

By a similar method, αKetoA, γKetoA, sKetoA, KetoB, γKetoB, αKetoB, sKetoB, rKetoB, KetoC, γKetoC, αKetoC, sKetoC, KetoRA, αHYA, γHYA, sHYA, rHYA, HYB, αHYB, γHYB, sHYB, rHYB, RA, HYC, αHYC, γHYC and sHYC were also measured for SREBP-1c, mature and immature SREBP-1 expression, SCD-1, FAS, ACC1, 2, intracellular triacylglycerol level, and antagonizing action on LXR by luciferase assay. As a result, γHYA, γKetoA, αKetoA, HYB, rHYB, RA, rKetoB also showed a lipid synthesis suppressive action by the antagonizing action on LXR.

From the above results, it was shown that HYA and KetoA from the fatty acids examined at this time have a strong lipid synthesis suppressive action by an antagonizing action on LXR. Similarly, rare fatty acids such as γHYA, γKetoA, αKetoA, HYB, rHYB, RA, rKetoB and the like were also shown to have a lipid synthesis suppressive action.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on a patent application No. 2012-237933 filed in Japan on Oct. 29, 2012, the contents of which are incorporated in full herein by reference.

INDUSTRIAL APPLICABILITY

The present invention has clarified oxo fatty acid and the like have a conventionally-unknown lipid and/or sugar and/or energy metabolism improving effect as a physiological function thereof. A lipid and/or sugar and/or energy metabolism improving agent containing the oxo fatty acid and the like is applicable to various fields such as pharmaceutical product, food, feed and the like, and the present invention is industrially extremely useful.

The invention claimed is:

1. A method of improving metabolism in a mammal, comprising administering an oxo fatty acid having 18 carbon atoms and a carbonyl group at the 10-position, and/or a hydroxy fatty acid having 18 carbon atoms and a hydroxyl group at the 10-position, or an agent comprising the same to the mammal.

2. The method according to claim 1, wherein the aforementioned oxo fatty acid and/or hydroxy fatty acid have/has a trans double bond at the 11-position, or a cis double bond at the 12-position.

3. The method according to claim 2, which is used for the improvement of at least one kind selected from the group consisting of obesity, diabetes, lipid metabolism abnormality, hyperlipidemia, and fatty liver.

4. The method according to claim 2, wherein the agent is a food or a food additive.

5. The method according to claim 2, wherein the agent is a pharmaceutical product.

6. The method according to claim 2, wherein the agent is a feed or a feed additive.

7. The method according to claim 1, wherein the oxo fatty acid is at least one kind selected from the group consisting of 10-oxo-cis-12-octadecenoic acid, 10-oxo-cis-12,cis-15-octadecadienoic acid, 10-oxo-cis-6,cis-12-octadecadienoic acid, 10-oxo-cis-6,cis-12,cis-15-octadecatrienoic acid, 10-oxooctadecanoic acid, 10-oxo-cis-6-octadecenoic acid, 10-oxo-cis-15-octadecenoic acid, 10-oxo-cis-6,cis-15-octadecadienoic acid, 10-oxo-trans-11-octadecenoic acid, 10-oxo-cis-6,trans-11-octadecadienoic acid, 10-oxo-trans-11,cis-15-octadecadienoic acid, and 10-oxo-cis-6,trans-11,cis-15-octadecatrienoic acid.

8. The method according to claim 7, which is used for the improvement of at least one kind selected from the group consisting of obesity, diabetes, lipid metabolism abnormality, hyperlipidemia, and fatty liver.

9. The method according to claim 7, wherein the agent is a food or a food additive.

10. The method according to claim 7, wherein the agent is a pharmaceutical product.

11. The method according to claim 7, wherein the agent is a feed or a feed additive.

12. The method according to claim 1, wherein the hydroxy fatty acid is at least one kind selected from the group consisting of 10-hydroxy-cis-12-octadecenoic acid, 10-hydroxy-cis-12,cis-15-octadecadienoic acid, 10-hydroxy-cis-6,cis-12-octadecadienoic acid, 10-hydroxy-cis-6,cis-12,cis-15-octadecatrienoic acid, 10-hydroxyoctadecanoic acid, 10-hydroxy-cis-15-octadecenoic acid, 10-hydroxy-cis-6-octadecenoic acid, 10-hydroxy-cis-6,cis-15-octadecadienoic acid, 10-hydroxy-trans-11-octadecenoic acid, 10-hydroxy-trans-11,cis-15-octadecadienoic acid, 10-hydroxy-cis-6,trans-11-octadecadienoic acid, and 10-hydroxy-cis-6,trans-11,cis-15-octadecatrienoic acid.

13. The method according to claim 12, which is used for the improvement of at least one kind selected from the group consisting of obesity, diabetes, lipid metabolism abnormality, hyperlipidemia, and fatty liver.

14. The method according to claim 12, wherein the agent is a food or a food additive.

15. The method according to claim 12, wherein the agent is a pharmaceutical product.

16. The method according to claim 12, wherein the agent is a feed or a feed additive.

17. The method according to claim 1, which is used for the improvement of at least one kind selected from the group consisting of obesity, diabetes, lipid metabolism abnormality, hyperlipidemia, and fatty liver.

18. The method according to claim 1, wherein the agent is a food or a food additive.

19. The method according to claim 1, wherein the agent is a pharmaceutical product.

20. The method according to claim 1, wherein the agent is a feed or a feed additive.

* * * * *

SEQUENCE LISTING

<160> NUMBER OF SEQ ID NOS: 14

<210> SEQ ID NO 1
<211> LENGTH: 654
<212> TYPE: DNA
<213> ORGANISM: Lactobacillus plantarum

```
<220> FEATURE:
<221> NAME/KEY: CDS
<222> LOCATION: (1)..(654)

<400> SEQUENCE: 1 atg tca gaa gca gtg aaa aat ttg gtg aac aat gat tta gca gac gtg      48
Met Ser Glu Ala Val Lys Asn Leu Val Asn Asn Asp Leu Ala Asp Val
1               5                   10                  15 atg ttt aac cgc cat tca gtt cgg cag ttt gac ccg aac gtt aaa att      96
Met Phe Asn Arg His Ser Val Arg Gln Phe Asp Pro Asn Val Lys Ile
            20                  25                  30 gga cgt gat gag tta caa aag atg att gcg gaa gca gcc acc gcg cca     144
Gly Arg Asp Glu Leu Gln Lys Met Ile Ala Glu Ala Ala Thr Ala Pro
        35                  40                  45 tcg gca tgt aat tta cag tca tgg cac ttt gtc gtc gtg gat acc ccc     192
Ser Ala Cys Asn Leu Gln Ser Trp His Phe Val Val Val Asp Thr Pro
50                  55                  60 gag gca aag gct aag ttc aaa caa gcc gtg atg aaa ttc aac tac cca     240
Glu Ala Lys Ala Lys Phe Lys Gln Ala Val Met Lys Phe Asn Tyr Pro
65                  70                  75                  80 cag gtc gac agt gca tcg gcc atc gtc ttt att gcc ggt gac acc cag     288
Gln Val Asp Ser Ala Ser Ala Ile Val Phe Ile Ala Gly Asp Thr Gln
                85                  90                  95 tcg cat tat gtt tat cgc gat gtc tgg aac aaa gtt tat gag gat ggg     336
Ser His Tyr Val Tyr Arg Asp Val Trp Asn Lys Val Tyr Glu Asp Gly
            100                 105                 110 aat att acg aag gaa cgc ttg gat cag att ctg gga acc ttc tta cca     384
Asn Ile Thr Lys Glu Arg Leu Asp Gln Ile Leu Gly Thr Phe Leu Pro
        115                 120                 125 tta tat gaa aat gcc aca cca gat ttc ttg aaa ttc gat gcg acg att     432
Leu Tyr Glu Asn Ala Thr Pro Asp Phe Leu Lys Phe Asp Ala Thr Ile
130                 135                 140 gat tgt tcc gtt gtc ggg atg cag ttg ctg cta gtg gca cgg gct cat     480
Asp Cys Ser Val Val Gly Met Gln Leu Leu Leu Val Ala Arg Ala His
145                 150                 155                 160 ggg tat gat gcc aat gcg ttc tcc gga att gac ttt gaa aag atg att     528
Gly Tyr Asp Ala Asn Ala Phe Ser Gly Ile Asp Phe Glu Lys Met Ile
                165                 170                 175 ccg acg ctg ggt ctt gat cct aaa cga tac gtg cca gta atg ggg atc     576
Pro Thr Leu Gly Leu Asp Pro Lys Arg Tyr Val Pro Val Met Gly Ile
            180                 185                 190 gca atc ggg aaa gca gcg caa gaa ccg ctc cat acg act cgg tac gat     624
Ala Ile Gly Lys Ala Ala Gln Glu Pro Leu His Thr Thr Arg Tyr Asp
        195                 200                 205 gcc aaa aca cag act gat ttc tta gcc taa                             654
Ala Lys Thr Gln Thr Asp Phe Leu Ala
210                 215

<210> SEQ ID NO 2
<211> LENGTH: 217
<212> TYPE: PRT
<213> ORGANISM: Lactobacillus plantarum

<400> SEQUENCE: 2

Met Ser Glu Ala Val Lys Asn Leu Val Asn Asn Asp Leu Ala Asp Val
1               5                   10                  15

Met Phe Asn Arg His Ser Val Arg Gln Phe Asp Pro Asn Val Lys Ile
            20                  25                  30

Gly Arg Asp Glu Leu Gln Lys Met Ile Ala Glu Ala Ala Thr Ala Pro
        35                  40                  45
```

-continued

Ser Ala Cys Asn Leu Gln Ser Trp His Phe Val Val Asp Thr Pro
 50                  55                  60

Glu Ala Lys Ala Lys Phe Lys Gln Ala Val Met Lys Phe Asn Tyr Pro
 65                  70                  75                  80

Gln Val Asp Ser Ala Ser Ala Ile Val Phe Ile Ala Gly Asp Thr Gln
                 85                  90                  95

Ser His Tyr Val Tyr Arg Asp Val Trp Asn Lys Val Tyr Glu Asp Gly
                100                 105                 110

Asn Ile Thr Lys Glu Arg Leu Asp Gln Ile Leu Gly Thr Phe Leu Pro
            115                 120                 125

Leu Tyr Glu Asn Ala Thr Pro Asp Phe Leu Lys Phe Asp Ala Thr Ile
130                 135                 140

Asp Cys Ser Val Val Gly Met Gln Leu Leu Val Ala Arg Ala His
145                 150                 155                 160

Gly Tyr Asp Ala Asn Ala Phe Ser Gly Ile Asp Phe Glu Lys Met Ile
                165                 170                 175

Pro Thr Leu Gly Leu Asp Pro Lys Arg Tyr Val Pro Val Met Gly Ile
            180                 185                 190

Ala Ile Gly Lys Ala Ala Gln Glu Pro Leu His Thr Thr Arg Tyr Asp
        195                 200                 205

Ala Lys Thr Gln Thr Asp Phe Leu Ala
210                 215

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3 ggagggtag ggccaacggc ct        22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
catgtcttcg aaagtgcaat cc        22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tggtttcact tggagctgtg        20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6

```
ggccttggag actttcttcc                                               20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
acagggacaa cctggagttc t                                             21

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
ctgtggtccc acttgatgag t                                             21

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
atcccgtacc ttcttctact g                                             21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
cccaaacata agccttcact g                                             21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ctctgaccat gttcgttctc                                               20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
atcttcatca cctccatctc                                               20

<210> SEQ ID NO 13
<211> LENGTH: 23
<212> TYPE: DNA
<213> ORGANISM: Artificial Sequence
```

-continued

```
<220> FEATURE:
<223> OTHER INFORMATION: Primer

<400> SEQUENCE: 13
taagtccctg ccctttgtac aca                                               23

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gatccgaggg cctcactaaa c                                                 21
```